United States Patent [19]

Larson

[11] 4,301,154

[45] Nov. 17, 1981

[54] INSECTICIDAL SYNERGISTIC MIXTURES OF O,O-DIETHYL O-(3,5,6-TRICHLORO-2-PYRIDINYL)PHOSPHOROTHIOATE AND 3-(2,2-DICHLOROETHENYL)-2,2-DIMETHYLCYCLOPROPANE CARBOXYLIC ACID:CYANO(6-PHENOXY-2-PYRIDINYL)-METHYL ESTER

[75] Inventor: Larry L. Larson, Concord, Calif.

[73] Assignee: The Dow Chemical Company, Midland, Mich.

[21] Appl. No.: 80,960

[22] Filed: Oct. 1, 1979

[51] Int. Cl.$^3$ .................. A01N 43/40; A01N 57/00; A01N 57/26

[52] U.S. Cl. .................................... 424/200; 424/263

[58] Field of Search .............................. 424/200, 263

[56] References Cited

U.S. PATENT DOCUMENTS

| | | | |
|---|---|---|---|
| 3,244,586 | 4/1966 | Rigterink | 424/200 |
| 3,818,019 | 6/1974 | Rigterink | 424/200 |
| 4,049,460 | 9/1977 | Broadbent | 424/200 |
| 4,100,297 | 7/1978 | Grandadam et al. | 424/306 |
| 4,144,331 | 3/1979 | Felton et al. | 424/304 |
| 4,163,787 | 8/1979 | Malhotra et al. | 424/263 |
| 4,171,355 | 10/1979 | Stubbs et al. | 424/304 |
| 4,210,642 | 7/1980 | Bock et al. | 424/200 |

FOREIGN PATENT DOCUMENTS

| | | |
|---|---|---|
| 2615646 | 10/1976 | Fed. Rep. of Germany ...... 424/304 |
| 2757768 | 6/1978 | Fed. Rep. of Germany . |
| 3861 | 6/1977 | South Africa . |
| 5073 | 8/1977 | South Africa . |
| 3712 | 1/1978 | South Africa . |

*Primary Examiner*—Douglas W. Robinson
*Attorney, Agent, or Firm*—S. Preston Jones; Ronald G. Brookens

[57] ABSTRACT

Insecticidal compositions containing a mixture of O,O-diethyl O-(3,5,6-trichloro-2-pyridinyl)phosphorothioate and 3-(2,2-dichloroethenyl)-2,2-dimethylcyclopropane carboxylic acid:cyano(6-phenoxy-2-pyridinyl)methyl ester are disclosed. Such compositions are useful in the kill and control of insects, particularly insects of the Lepidoptera order and especially of the genus Heliothis.

7 Claims, No Drawings

INSECTICIDAL SYNERGISTIC MIXTURES OF 0,0-DIETHYL 0-(3,5,6-TRICHLORO-2-PYRIDINYL)PHOSPHOROTHIOATE AND 3-(2,2-DICHLOROETHENYL)-2,2-DIMETHYLCYCLOPROPANE CARBOXYLIC ACID:CYANO(6-PHENOXY-2-PYRIDINYL)-METHYL ESTER

SUMMARY OF THE INVENTION

The present invention is directed to new insecticidal compositions which are useful in the kill and control of insects particularly insects of the Lepidoptera order and especially of the genus Heliothis. These compositions comprise mixtures of O,O-diethyl O-(3,5,6-trichloro-2-pyridinyl)phosphorothioate and 3-(2,2-dichloroethenyl)-2,2-dimethylcyclopropane carboxylic acid:-cyano(6-phenoxy-2-pyridinyl)methyl ester. It has been found that the toxic ingredients of said compositions are mutually activating.

The O,O-diethyl O-(3,5,6-trichloro-2-pyridinyl)phosphorothioate employed in accordance with the teachings of the present invention is a solid material melting at ~41°-42° C. The compound, its method of preparation and its insecticidal activity are taught in U.S. Pat. No. 3,244,586.

The 3-(2,2-dichloroethenyl)-2,2-dimethylcyclopropane carboxylic acid:cyano(6-phenoxy-2-pyridinyl)-methyl ester employed in accordance with the teachings of the present invention is a liquid material boiling at ~190°-200° C. under 0.1-0.2 mm Hg and has a refractive index of $n_D^{20}$ of 1.5264. The compound, its method of preparation and its insecticidal activity are taught in U.S. Pat. No. 4,163,787.

The new insecticidal composition of the present invention comprises about 1 part by weight of O,O-diethyl O-(3,5,6-trichloro-2-pyridinyl)phosphorothioate and from about 1/133 to about 1 part by weight of 3-(2,2-dichloroethenyl)-2,2-dimethylcyclopropane, i.e. a ratio of about 133:1 to about 1:1. A preferred ratio is from about 2:1 to about 133:1 with the most preferred ratio being from about 2:1 to about 33:1.

These insecticidal compositions are especially effective in killing and controlling insects, particularly Lepidoptera, especially Heliothis species, which infest crops such as corn, soybeans, tobacco and particularly cotton.

The mixtures of active compounds of the present invention have been found to possess good activity against Heliothis species. Accordingly, the present invention also comprises methods for controlling such insects and/or their habitats with a pesticidally effective amount of the active compound mixture. For such uses the unmodified active materials of the present invention can be employed. However, the present invention embraces the use of an insecticidally-effective amount of the active materials in admixture with an inert material, as an adjuvant or carrier therefor, in solid or liquid form. Thus, for example, the active mixture can be dispersed on a finely divided solid and employed therein as a dust. Also, the active mixture, as liquid concentrates or solid compositions comprising the active mixture, can be dispersed in water, typically with the aid of a wetting agent, and the resulting aqueous dispersion employed as a spray. In other procedures, the active mixture can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid pesticidal formulations similarly are well known to the skilled artisan.

As organic solvents used as extending agents there can be employed hydrocarbons, e.g. benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl carbitol acetate and glycerine. Mixtures of water and organic solvents, either as solutions or emulsions, can be employed.

The active mixtures can also be applied as aerosols, e.g., by dispersing them in air by means of a compressed gas such as dichlorodifluoromethane or trichlorofluoromethane and other such materials.

The active mixture of the present invention can also be applied with adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di(2-ethylhexyl)-ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylene)-sorbitan monostearate (Tween 60), and sodium dihexyl sulfosuccinate.

The concentration of the active mixtures in liquid formulations generally is from about 0.01 to about 95 percent by weight or more. Concentrations of from about 0.1 to about 50 weight percent are often employed. In formulations to be employed as concentrates, the active materials can be present in a concentration of from about 5 to about 98 weight percent. In dusts or dry formulations, the concentration of the active ingredient can be from about 0.01 to about 95 weight percent or more; concentrations of from about 0.1 to about 50 weight percent are often conveniently employed. The active compositions can also contain other compatible additaments, for example, plant growth regulants, pesticides and the like.

The present compositions can be applied by the use of power-dusters, boom and hand sprayers, spray-dusters and by other conventional means. The compositions can also be applied from airplanes as a dust or a spray.

The active mixtures of this invention are usually applied at an approximate rate of from about 1/16 pound to about 5 pounds or more per acre, but lower or higher rates may be appropriate in some cases. A preferred application rate is from ½ pound to about 2 pounds per acre.

O,O-diethyl O-(3,5,6-trichloro-2-pyridinyl)phosphorothioate and 3-(2,2-dichloroethenyl)-2,2-dimethylcyclopropane carboxylic acid:cyano(6-phenoxy-2-pyridinyl)methyl ester in the control of Heliothis insects.

Test solutions were prepared by admixing predetermined amounts of each of the above compounds in predetermined amounts of water containing predetermined amounts of acetone and Triton X155 surfactant.

Tobacco leaf discs, 3 inches in diameter were dipped into one of the above mixtures and placed in an open petri dish to dry. After the leaf discs were dry, 5 late second instar (approximately 3-day old) tobacco bud worms (*Heliothis virescens*) were placed in each dish and the dishes covered. All treatments were run in triplicate and on two different days. Mortality was recorded 48 hours after treatment with moribund larvae unable to crawl their own body length being counted as dead. In this test method, intoxication occurred through contact with and feeding upon treated plants.

The results of this study are set forth below in Table I.

TABLE I

| Test No.[1] | Chemical[2] | Amount in PPM | Chemical[3] | Amount in PPM | Ratio of A to B | Expected Control in Percent[4] | Actual Control in Percent | Percent Increase Over Expected Control[5] |
| --- | --- | --- | --- | --- | --- | --- | --- | --- |
| 1 | — | — | — | — | — | — | 0 | — |
| 2 | A | 12.5 | — | — | — | — | 3 | — |
| 3 | A | 25 | — | — | — | — | 13 | — |
| 4 | A | 50 | — | — | — | — | 30 | — |
| 5 | A | 100 | — | — | — | — | 60 | — |
| 6 | — | — | B | 0.75 | — | — | 7 | — |
| 7 | — | — | B | 1.5 | — | — | 13 | — |
| 8 | — | — | B | 3.1 | — | — | 27 | — |
| 9 | — | — | B | 6.2 | — | — | 40 | — |
| 10 | — | — | B | 12.5 | — | — | 67 | — |
| 11 | A | 12.5 | B | 0.75 | 16:1 | 9 | 10 | 2 |
| 12 | A | 12.5 | B | 1.5 | 8:1 | 16 | 23 | 44 |
| 13 | A | 12.5 | B | 3.1 | 4:1 | 29 | 37 | 28 |
| 14 | A | 12.5 | B | 6.2 | 2:1 | 42 | 67 | 60 |
| 15 | A | 12.5 | B | 12.5 | 1:1 | 68 | 70 | 3 |
| 16 | A | 25 | B | 0.75 | 33:1 | 19 | 27 | 42 |
| 17 | A | 25 | B | 1.5 | 16:1 | 24 | 43 | 79 |
| 18 | A | 25 | B | 3.1 | 8:1 | 36 | 50 | 39 |
| 19 | A | 25 | B | 6.2 | 4:1 | 48 | 63 | 31 |
| 20 | A | 25 | B | 12.5 | 2:1 | 71 | 90 | 27 |
| 21 | A | 50 | B | 0.75 | 66:1 | 35 | 40 | 14 |
| 22 | A | 50 | B | 1.5 | 33:1 | 39 | 53 | 36 |
| 23 | A | 50 | B | 3.1 | 16:1 | 49 | 70 | 43 |
| 24 | A | 50 | B | 6.2 | 8:1 | 58 | 70 | 21 |
| 25 | A | 50 | B | 12.5 | 4:1 | 77 | 93 | 21 |
| 26 | A | 100 | B | 0.75 | 133:1 | 66 | 77 | 17 |
| 27 | A | 100 | B | 1.5 | 66:1 | 65 | 73 | 12 |
| 28 | A | 100 | B | 3.1 | 33:1 | 71 | 90 | 27 |
| 29 | A | 100 | B | 6.2 | 16:1 | 76 | 87 | 14 |
| 30 | A | 100 | B | 12.5 | 8:1 | 87 | 100 | 15 |

[1]Test Nos. 1–10 are control runs with Test 1 being a no chemical control (surfactant/acetone/water alone).
[2]Chemical A represents O,O-diethyl O-(3,5,6-trichloro-2-pyridinyl)phosphorothioate.
[3]Chemical B represents 3-(2,2-dichloroethenyl)-2,2-dimethylcyclopropane carboxylic acid:cyano(6-phenoxy-2-pyridinyl)methyl ester.
[4]Expected control equals % control by chemical A + % control by chemical B minus (−)
$$\frac{\% \text{ control by chemical A} \times \% \text{ control chemical B}}{100}$$
[5]Percent increase over expected control equals $\frac{\text{actual control}}{\text{expected control}} \times 100 - 100$

DESCRIPTION OF THE PREFERRED EMBODIMENTS

The following examples illustrate the present invention and the manner by which it can be practiced but, as such, should not be construed as limitations upon the overall scope of the same.

EXAMPLE I

A study was conducted to determine the effectiveness and synergistic response of various combinations of Data from Table I illustrates that better control was obtained employing the two toxicants together than would be expected from the results obtained from employing each of the two toxicants alone. These data are obtained according to the technique described in Colby, "Calculating Synergistic and Antagonistic Responses of Herbicide Combinations", Weeds, Vol. 15 (1967) pages 20–22 and Colby, "Greenhouse Evaluation of Herbicide Combinations", Proc. NEWCC, No. 19, pages 312–320.

What is claimed is:

1. A synergistic insecticidal composition which comprises an inert carrier and an insecticidally effective amount of an active mixture of toxicants consisting essentially of about 1 part by weight of O,O-diethyl O-(3,5,6-trichloro-2-pyridinyl)phosphorothioate and from about 1/133 to about 1 part by weight of 3-(2,2-dichloroethenyl)-2,2-dimethylcyclopropane carboxylic acid:cyano(6-phenoxy-2-pyridinyl)methyl ester.

2. The composition as defined in claim 1 wherein the carrier is an inert liquid carrier.

3. The composition as defined in claim 2 wherein the active mixture of toxicants is present in an amount of from about 5 to about 95 percent by weight of the total composition.

4. The composition as defined in claim 2 wherein the composition is present as an aqueous dispersion and the mixture of toxicants is present in an amount of from about 0.01 to about 50 percent by weight of the total composition.

5. A method for killing and controlling insects which comprises contacting said insects or their habitat with an insecticidally effective amount of a composition which comprises an inert carrier and an active mixture of toxicants consisting essentially of about one part by weight of O,O-diethyl O-(3,5,6-trichloro-2-pyridinyl)-phosphorothioate and from about 1/133 to about 1 part by weight of 3-(2,2-dichloroethenyl)-2,2-dimethylcyclopropane carboxylic acid:cyano(6-phenoxy-2-pyridinyl)methyl ester.

6. The method as defined in claim 5 wherein the insects are of the genus Heliothis.

7. The method as defined in claim 5 wherein the composition is employed in amounts of from about 1/16 pound to about 5 pounds per acre.

* * * * *